United States Patent
Benavitz et al.

(10) Patent No.: US 10,194,899 B2
(45) Date of Patent: Feb. 5, 2019

(54) SYSTEMS AND METHODS FOR ACROMIOCLAVICULAR STABILIZATION

(71) Applicant: Arthrex, Inc., Naples, FL (US)

(72) Inventors: William C. Benavitz, Naples, FL (US); Allen E. Holowecky, Naples, FL (US); Augustus D. Mazzocca, West Hartford, CT (US); Eugene M. Wolf, San Rafael, CA (US); James J. Guerra, Naples, FL (US)

(73) Assignee: Arthrex, Inc., Naples, FL (US)

( * ) Notice: Subject to any disclaimer, the term of this patent is extended or adjusted under 35 U.S.C. 154(b) by 567 days.

(21) Appl. No.: 14/925,529

(22) Filed: Oct. 28, 2015

(65) Prior Publication Data

US 2017/0119366 A1     May 4, 2017

(51) Int. Cl.
*A61F 5/00*     (2006.01)
*A61B 17/04*    (2006.01)
*A61B 17/16*    (2006.01)
*A61B 17/06*    (2006.01)

(52) U.S. Cl.
CPC .... *A61B 17/0401* (2013.01); *A61B 17/06166* (2013.01); *A61B 17/1684* (2013.01); *A61B 2017/044* (2013.01); *A61B 2017/0404* (2013.01); *A61B 2017/0445* (2013.01)

(58) Field of Classification Search
CPC .......... A61B 17/1684; A61B 17/06166; A61B 17/1778; A61B 17/0401
USPC ........................................................ 606/87
See application file for complete search history.

(56) References Cited

U.S. PATENT DOCUMENTS

| | | |
|---|---|---|
| 8,162,997 B2 | 4/2012 | Struhl |
| 8,753,375 B2 | 6/2014 | Albertorio |
| 8,795,293 B2 | 8/2014 | Petersen et al. |
| 8,876,900 B2 | 11/2014 | Guederian et al. |
| 8,926,661 B2 | 1/2015 | Sikora et al. |
| 9,005,245 B2 | 4/2015 | Thornes et al. |
| 9,072,510 B2 | 7/2015 | Thornes et al. |
| 2007/0270804 A1* | 11/2007 | Chudik ............ A61B 17/06166 606/60 |
| 2007/0270822 A1 | 11/2007 | Heinz |

(Continued)

FOREIGN PATENT DOCUMENTS

| | | |
|---|---|---|
| CA | 2 785 039 A1 | 4/2011 |
| WO | WO 2004/112650 A2 | 12/2004 |
| WO | WO 2011/040917 A1 | 4/2011 |

OTHER PUBLICATIONS

Garcia, et al. "Anatomic approach to reconstruction of the unstable acromioclavicular joint", No. 1, vol. 21, Special Focus, Jan./Feb. 2010, pp. 43-48.

*Primary Examiner* — Si Ming Ku
(74) *Attorney, Agent, or Firm* — Blank Rome LLP

(57) ABSTRACT

Surgical methods for stabilizing a joint are disclosed. The methods aid in surgical repairs by allowing for quick and reproducible repairs to be made. A bone tunnel is formed anteriorly/posteriorly in clavicle, and a bone tunnel is formed superiorly in acromion. At least one cannulated insert is provided into one or both of bone tunnels to protect the bone from abrasions caused by a flexible construct. A flexible construct is passed through the acromion tunnel and the clavicle tunnel. An attachment device may then be positioned on at least one side of the clavicle and/or acromion tunnel, and the flexible construct is attached to the attachment device.

13 Claims, 2 Drawing Sheets

(56) References Cited

U.S. PATENT DOCUMENTS

| | | | |
|---|---|---|---|
| 2010/0256677 A1* | 10/2010 | Albertorio | A61B 17/0401 606/232 |
| 2010/0262185 A1 | 10/2010 | Gelfand et al. | |
| 2013/0006303 A1 | 1/2013 | Petersen et al. | |
| 2013/0172944 A1 | 7/2013 | Fritzinger et al. | |
| 2013/0331886 A1 | 12/2013 | Thomas | |
| 2015/0039031 A1 | 2/2015 | Sikora et al. | |

* cited by examiner (Top View)

SYSTEMS AND METHODS FOR ACROMIOCLAVICULAR STABILIZATION

BACKGROUND

The present disclosure relates to surgical methods and, more particularly, to surgical methods for acromioclavicular joint stabilization.

SUMMARY

Surgical methods for acromioclavicular joint stabilization are disclosed. Methods can comprise forming a first tunnel in a first bone of an acromioclavicular joint; forming a second tunnel in a second bone of the acromioclavicular joint; and securing a cannulated insert into at least one of the first and second tunnels. A method may further comprise passing a flexible construct through the first and second tunnels; positioning/placing an attachment device within or over at least one of the first and second tunnels; and affixing/securing a flexible construct to the attachment device.

DETAILED DESCRIPTION

Surgical methods for joint stabilization are disclosed. An exemplary method comprises inter alia the steps of: (i) forming a first tunnel in a first bone of a joint and forming a second tunnel in a second bone of the joint; (ii) securing (implanting or inserting) a cannulated insert into at least one of the first and second bone tunnels; and (iii) passing a flexible construct through the first and second bone tunnels. An exemplary method may further comprise (iv) positioning/inserting/placing an attachment device within or over at least one of the first and second bone tunnels; and (v) securing/fixating/affixing the flexible construct to the attachment device. In an exemplary embodiment, one of the first and second bones is the acromion, and the other of the first and second bones is the clavicle.

An exemplary method of acromioclavicular (AC) joint stabilization comprises inter alia the steps of: forming at least one clavicle tunnel through a clavicle; forming at least one acromion tunnel through an acromion; securing at least one cannulated insert into at least one of the clavicle and acromion tunnels; passing at least one flexible construct through each of the clavicle and acromion tunnels; placing at least one attachment device within or on at least one of the clavicle and acromion tunnels; and affixing the at least one flexible construct to the at least one attachment device. The at least one clavicle tunnel may be formed anteriorly or posteriorly through the clavicle, and the at least one acromion tunnel may be formed superiorly through the acromion. The at least one clavicle tunnel may be formed superiorly through the clavicle, and the at least one acromion tunnel may be formed superiorly through the acromion.

The flexible construct may be a suture, suture tape, suture chain, or any combination of suture, suture tape, and suture chain. The flexible construct may be a tensionable, knotless, adjustable, self-locking, construct formed of a length of flexible material with a knotless, adjustable, self-locking closed loop, a splice adjacent the closed loop, and a free end. The closed loop has an adjustable perimeter, or a fixed perimeter (i.e., an adjustable length or a fixed length of the loop). The flexible construct may be a suture strand such as FiberWire The attachment device may be a fixation device that allows securement of a flexible strand to it, for example, a button, a washer, an anchor, a screw, a bolt, or a nail, among many others. The attachment device may be secured/positioned at one of the clavicle and/or acromion tunnels The methods detailed below have applications to joint and ligament reconstruction and stabilization. Particular applications relate to AC joint stabilization, where the methods of the present invention provide simple, reproducible, minimally invasive techniques for AC joint stabilization.

Figure 1:
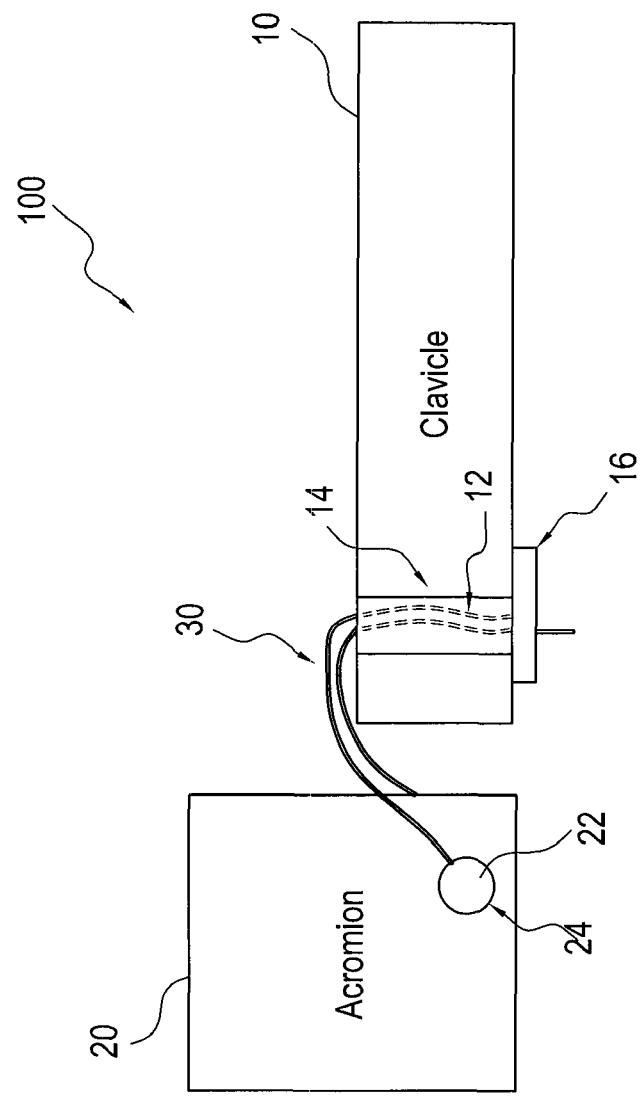
FIG. 1 illustrates an exemplary embodiment of an acromioclavicular joint repair.
Figure 2:
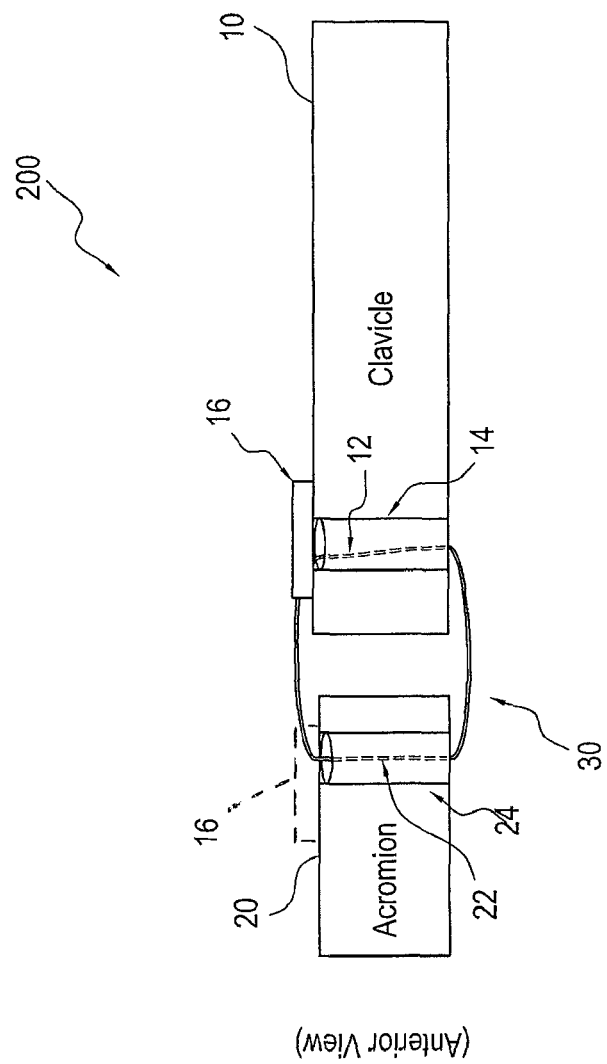
FIG. 2 illustrates another exemplary embodiment of an acromioclavicular joint repair.

Referring now to the drawings, where like elements are designated by like reference numerals, FIGS. 1 and 2 illustrate AC joint stabilizations 100 and 200 (repairs 100, 200) according to different embodiments.

FIG. 1 illustrates a top view of an exemplary embodiment of an AC joint stabilization 100 (repair 100). A first bone tunnel 12 is formed anteriorly/posteriorly in clavicle 10, and a second bone tunnel 22 is formed superiorly in acromion 20. At least one cannulated insert 14, 24 can be provided (for example, implanted, positioned, inserted, or secured) into one or both of bone tunnels 12 and 22. The at least one cannulated insert can protect the bone from abrasions caused by flexible construct 30.

Flexible construct 30 is passed through acromion tunnel 22 or acromion cannulated insert 24, and then passed through clavicle bone tunnel 12 or clavicle cannulated insert 14. Attachment device 16 may then be inserted on one side of clavicle bone tunnel 12. Alternatively, attachment device 16 may be preloaded with flexible construct 30. In that case, flexible construct 30 and attachment device 16 are inserted at the same time, and the flexible construct can pass through both tunnels before the ends of the strands are secured to attachment device 16.

Flexible construct 30 can be affixed to attachment device 16 by means known in the art, for example by passing through one or more apertures in attachment device 16 and tying a knot. In the exemplary embodiment illustrated in FIG. 1, one end of flexible construct 30 is passed through acromion bone tunnel 22 or acromion cannulated insert 24, then both ends are passed into clavicle bone tunnel 12 or clavicle cannulated insert 14 opposite of attachment device 16. Both ends are then secured to attachment device 16.

Bone tunnels 12 and 22 can be formed according to methods known in the art. For example, bone tunnels 12 and 22 can be formed by drilling through the target bone using a drill of the desired diameter. Alternatively, each bone tunnel can be formed by first drilling a drill guide wire through the target bone. A drill with the desired diameter is then guided over the drill wire guide to bore out each of the bone tunnels 12 and 22.

At least one cannulated insert may be affixed/inserted/secured/positioned or implanted into at least one of bone tunnels 12 and 22. In an embodiment, a clavicle cannulated insert 14 is implanted into clavicle tunnel 12, and no insert is implanted into acromion tunnel 22. In another embodiment, an acromion cannulated insert 24 is implanted into acromion tunnel 22, and no insert is implanted into clavicle tunnel 12. In another embodiment, a cannulated insert is implanted into both the clavicle tunnel 12 and acromion tunnel 22. In yet another embodiment, no insert is implanted in any tunnel. FIG. 1 illustrates an example embodiment having both a clavicle cannulated insert 14 implanted into clavicle tunnel 12, and acromion cannulated insert 24 implanted into acromion tunnel 22.

Cannulated inserts 14 and 24 can be any suitable cannulated inserts that can securely attach to bone and allow passage of flexible construct through a cannulated body. For example, cannulated inserts 14 and 24 can be cannulated screws having external bone fixation means to securely fix the screws in bone tunnels 12 and 22. Additionally, cannulated inserts 14 and 24 can be designed or chosen such that cannulated inserts 14 and 24 do not have a head or other portion substantially extending from bone tunnels 12 and 22. Cannulated inserts 14 and 24 can be implanted such that each end of cannulated inserts 14 and 24 is completely within bone tunnels 12 and 22, even or nearly even with entrances of bone tunnels 12 and 22, or extending insubstantially out from bone tunnels 12 and 22. FIG. 1 illustrates an exemplary embodiment having cannulated inserts 14 and 24 disposed completely within bone tunnels 12 and 22.

Attachment device 16 may be positioned/inserted within or on/above the bone tunnel(s) before or after flexible construct 30 is passed through the bone tunnels or cannulated inserts. Alternatively, attachment device 16 may be preloaded with flexible construct 30.

Attachment device 16 may be any suitable attachment or fixation device known in the art. For example, attachment device 16 may be a cortical button or washer, or a button in the shape of a "dog bone," or an anchor, or any other fixation/attachment device known in the art. Attachment device 16 may be any button, washer, anchor, screw, bolt, or nail, or combination of these fixation devices.

Flexible construct 30 may be any flexible strand or cord, or any length of a flexible material that can be passed through at least a portion of a bone tunnel or through-hole. For example, and as detailed below, the flexible construct may be at least one strand of suture, for example a high strength suture material such as FiberWire® suture, which is formed of an advanced, high-strength fiber material, namely ultrahigh molecular weight polyethylene (UHMWPE), or suture tape, suture chain, or any combination of suture, suture tape, and suture chain. Flexible construct 30 may be also any tensionable, knotless, adjustable, self-locking, construct formed of a length of flexible material (such as suture) with a knotless, adjustable, self-locking closed loop (having a fixed or adjustable perimeter), a splice adjacent the closed loop, and a free end. The knotless loop may be formed to encircle one bone (for example, one of the acromion or clavicle) with the free tensionable end exiting the other bone (for example, the other of the acromion or clavicle) to allow stabilization of the bones relative to each other and reduction in the distance between the two bones.

Flexible construct 30 is passed through acromion bone tunnel 22 and clavicle bone tunnel 12, and is secured to attachment device 16.

FIG. 2 illustrates an anterior view of another exemplary embodiment of an AC joint stabilization 200 (repair 200). Joint stabilization 200 differs from joint stabilization 100 in a number of ways, including how bone tunnel 12 is formed in clavicle 10, where attachment device 16 is implanted, and how flexible construct 30 is passed. The exemplary embodiment consists of forming a first bone tunnel 12 superiorly in clavicle 10 (instead of anteriorly/posteriorly), and forming a second bone tunnel 22 superiorly in acromion 20. At least one cannulated insert 14, 24 can be implanted into one or both of bone tunnels 12 and 22. FIG. 2 illustrates an exemplary embodiment having both a clavicle cannulated insert 14 implanted into clavicle bone tunnel 12, and an acromion cannulated insert 24 implanted into acromion bone tunnel 22, but it is understood that a cannulated insert may be implanted into clavicle bone tunnel 12 and not in acromion bone tunnel 22, or vice versa.

Flexible construct 30 is passed through acromion tunnel 22 or acromion cannulated insert 24, and then passed through clavicle bone tunnel 12 or clavicle cannulated insert 14. Attachment device 16 may then be positioned on one side of clavicle bone tunnel 12. Alternatively, attachment device 16 may be preloaded with flexible construct 30. In that case, flexible construct 30 and attachment device 16 are positioned/inserted at the same time, and the flexible construct can pass through both tunnels before the ends of the strands are secured to attachment device 16.

Flexible construct 30 can be secured/affixed to attachment device 16 by means known in the art, for example by passing through one or more apertures in attachment device 16 and tying a knot. In the exemplary embodiment illustrated by FIG. 2, one end of flexible construct 30 is passed through acromion bone tunnel 22 or acromion cannulated insert 24, then each end is passed into clavicle bone tunnel 12 or clavicle cannulated insert 14 from opposite sides and secured to attachment device 16.

An exemplary method of joint repair comprises the steps of: forming a first tunnel in a first bone of a joint; forming a second tunnel in a second bone of the joint; securing (for example, implanting) a cannulated insert into at least one of the first and second tunnels; passing a flexible construct through the first and second bone tunnels; providing (for example, inserting) an attachment device on one end of the first or second bone tunnel; and affixing the flexible construct to the attachment device. The first tunnel may be a clavicle tunnel formed anteriorly or posteriorly through a clavicle. The second tunnel may be an acromion tunnel formed superiorly through an acromion. The attachment device may be positioned at one end of the clavicle tunnel, and the method may further comprise: passing at least one end of the flexible construct through the acromion tunnel or acromion cannulated insert; and passing all ends of the flexible construct through an end of the clavicle tunnel opposite the attachment device.

The attachment device may be also inserted on one end of the acromion tunnel, and the method may comprise: passing at least one end of the flexible construct through the clavicle tunnel or clavicle cannulated insert; and passing all ends of the flexible construct through an end of the acromion tunnel opposite the attachment device.

The first bone tunnel may be also a clavicle tunnel formed superiorly through a clavicle. The second bone tunnel may be an acromion tunnel formed superiorly through an acromion. The attachment device may be inserted on one end of the clavicle tunnel, and the method may further comprise: passing at least one end of the flexible construct through the acromion tunnel or acromion cannulated insert; and passing at least one end of the flexible construct through opposite ends of the clavicle tunnel. The attachment device may be positioned at one end of the acromion tunnel, and the method may further comprise: passing at least one end of the flexible construct through the clavicle tunnel or clavicle cannulated insert; and passing at least one end of the flexible construct through opposite ends of the acromion tunnel.

The present invention can include numerous variations to the exemplary embodiments described above. For example, the exemplary embodiments described above can be modified to include forming two or more bone tunnels in clavicle 10, acromion 20, or both. A cannulated insert can be implanted into any or all of the additional bone tunnels. If additional bone tunnels are formed, then flexible construct may be passed in a crossed or bridged configuration. Furthermore, additional flexible constructs may be used.

In any embodiment, more than one attachment device 16 may be used. In example embodiments having one clavicle bone tunnel 12, an attachment device may be positioned at both ends of clavicle bone tunnel 12. If two or more bone tunnels are formed in clavicle 10, then an attachment device can be affixed to any end of any clavicle bone tunnel, so long as at least one attachment device is used.

Attachment device 16 may alternatively be positioned at one end of acromion bone tunnel 22 instead of clavicle tunnel 12. In this embodiment, flexible construct 30 can be passed through clavicle bone tunnel 12 or clavicle cannulated insert 14 first, and then through acromion bone tunnel 22 or acromion cannulated insert 24 prior to being secured to attachment device 16. Furthermore, an attachment device may be positioned at each end of acromion bone tunnel 22. If two or more bone tunnels are formed in acromion 20, then an attachment device can be affixed to any end of any acromion bone tunnel, so long as at least one attachment device is used.

Attachment device 16 detailed above may be any suitable fixation device known in the art. For example, attachment device 16 may be a cortical button or washer, or a button in the shape of a "dog bone," such as the button disclosed and described in US 2012/0150203, published Jun. 14, 2012, the disclosure of which is fully incorporated by reference in its entirety herein. Attachment device 16 may also be a cortical button or washer, such as those disclosed and described in U.S. Pat. No. 8,876,900, issued Nov. 4, 2014; U.S. Pat. No. 8,162,997, issued Apr. 24, 2012; U.S. Pat. No. 9,005,245, issued Apr. 14, 2015; and U.S. Pat. No. 9,072,510, issued Jul. 7, 2015, the disclosures of all of which are fully incorporated by reference in their entirety herein. Attachment device 16 may be a cannulated anchor, such as the anchor disclosed and described in US 2013/0023929, published Jan. 24, 2013, the disclosure of which is fully incorporated by reference in its entirety herein. In an embodiment using such an anchor, a cannulated insert may not be necessary in the bone tunnel receiving the anchor. However, depending on the depth of the bone tunnel and the anchor, a cannulated insert may still be wanted or needed.

Attachment device 16 may be circular, oblong, or any other suitable geometry. Attachment device 16 may be formed, for example, of metals such as titanium, titanium alloys or stainless steel, PEEK or PLLA, or other biocompatible and/or bioabsorbable materials known in the art. Attachment device 16 may comprise at least one aperture through which one or more end of flexible construct 30 may pass or secure to.

Flexible construct 30 is passed through acromion bone tunnel 22 and clavicle bone tunnel 12, and is secured to attachment device 16. Flexible construct 30 may be formed of suture or suture-like material, for example a high strength suture material such as FiberWire® suture, sold by Arthrex, Inc. of Naples, Fla., and described in U.S. Pat. No. 6,716,234, issued Apr. 6, 2004, the disclosure of which is fully incorporated by reference in its entirety herein. The high strength suture may be available in various lengths. FiberWire® suture is formed of an advanced, high-strength fiber material, namely ultrahigh molecular weight polyethylene (UHMWPE), sold under the tradenames SPECTRA® (Honeywell) and DYNEEMA® (DSM), braided with at least one other fiber, natural or synthetic, to form lengths of suture material. The suture may optionally include filaments of various colors. The suture may be also formed of a plurality of suture strands configured to separate from a single strand to a plurality of strands and/or loops.

Flexible construct 30 may also be formed of a suture tape, for example, Arthrex FiberTape®, which is a high strength suture tape that is braided and rectangular-like in cross section and as disclosed in U.S. Pat. No. 7,892,256, issued Feb. 22, 2011, the disclosure of which is fully incorporated by reference in its entirety herein. However, the surgical methods can be used with any type of flexible material or suture known in the art.

Flexible construct 30 may be also in the form of a tensionable construct that can be attached to tissue (passed through or around tissue, for example, bone to be fixated/approximated to another bone). The tensionable construct may be in the form of a tensionable, knotless, adjustable, self-locking, construct formed of a length of flexible material (such as suture) with a knotless, adjustable, self-locking closed loop (having a fixed or adjustable perimeter), a splice adjacent the closed loop, and a free end.

Although the present invention has been described above with reference to a flexible construct comprising FiberWire® suture and/or FiberTape® suture tape, the invention contemplates any flexible material including hollow braided constructs, or filaments of various colors, among many others. Furthermore, the invention contemplates using a flexible construct such as the one described in US 2013/0023929, published Jan. 24, 2013, the disclosure of which is fully incorporated by reference in its entirety herein. The flexible construct described therein contains two suture splices that are self-cinching (similar to the suture splices used in adjustable suture button/loop construct described in U.S. Pat. No. 8,460,379, issued Jun. 11, 2013; and U.S. Pat. No. 8,439,976, issued May 14, 2013, both sold by Arthrex, Inc. under the tradename ACL TightRope®, the disclosure of both of which are incorporated by reference in their entirety herewith). The lead loops of the suture are weaved through a suture loop (e.g., an Arthrex FiberLink®). The remaining suture and splices are weaved on the opposite side of the suture loop.

US 2013/0023929 describes a flexible construct formed of suture together with loops and a shuttle/pull suture (for example, a FiberLink®) or a nitinol loop which is attached to the suture construct to allow shuttling of the flexible construct through the tunnels in the clavicle and acromion. The FiberLink® is attached to the two lead loops of the suture. Free suture ends can be exposed outside an attachment device to allow tensioning after implantation. The flexible construct comprises a knotless, adjustable, flexible loop which has an adjustable length and can be attached to an attachment device. Details and the formation of the suture splices of the knotless, self-locking, adjustable construct are set forth, for example, in U.S. Pat. No. 8,460,379, issued Jun. 11, 2013; and U.S. Pat. No. 8,439,976, issued May 14, 2013, the disclosure of both of which are incorporated by reference in their entirety herein.

The flexible construct may be coated (partially or totally) with wax (beeswax, petroleum wax, polyethylene wax, or others), silicone, silicone rubbers, PTFE (Teflon, Hostaflon, or others), PBA (polybutylate acid), ethyl cellulose (Filodel) or other coatings, to improve lubricity of the suture or tape, knot security, pliability, handleability, or abrasion resistance, for example. The flexible construct may also contain a bioabsorbable material, such as PLLA or one of the other polylactides, for example, and/or may be formed of twisted fibers having strands of a contrasting color added to the braided threads, to make the suture more visible during surgical procedures. The colored strands can be dyed filaments or strands, for example.

What is claimed is:

1. A method of acromioclavicular joint stabilization, comprising:
   forming at least one clavicle tunnel through a clavicle;
   forming at least one acromion tunnel through an acromion;
   securing at least one cannulated insert into each one of the clavicle and acromion tunnels;
   passing at least one flexible construct through each of the clavicle and acromion tunnels;
   placing at least one attachment device within or on at least one of the clavicle and acromion tunnels after the step of securing the at least one cannulated insert; and
   affixing the at least one flexible construct to the at least one attachment device.

2. The method of claim 1, wherein the at least one attachment device is secured at an end of the at least one clavicle tunnel.

3. The method of claim 1, wherein the at least one attachment device is secured at an end of the at least one acromion tunnel.

4. The method of claim 1, wherein the flexible construct is a suture, suture tape, suture chain, or any combination of suture, suture tape, and suture chain.

5. The method of claim 1, wherein the flexible construct is a tensionable, knotless, adjustable, self-locking, construct formed of a length of flexible material with a knotless, adjustable, self-locking closed loop, a splice adjacent the closed loop, and a free end.

6. The method of claim 5, wherein the flexible material is coreless suture that allows splicing.

7. The method of claim 5, wherein the closed loop has an adjustable perimeter.

8. The method of claim 5, wherein the closed loop has a fixed perimeter.

9. The method of claim 1, wherein the attachment device is a button, a washer, an anchor, a screw, a bolt, or a nail.

10. The method of claim 1, further comprising:
    forming the at least one clavicle tunnel anteriorly or posteriorly through the clavicle; and
    forming the at least one acromion tunnel superiorly through the acromion.

11. The method of claim 1, further comprising:
    forming the at least one clavicle tunnel superiorly through the clavicle; and
    forming the at least one acromion tunnel superiorly through the acromion.

12. A method of acromioclavicular joint stabilization comprising:
    forming one clavicle tunnel through the clavicle;
    forming one acromion tunnel through the acromion;
    securing one cannulated insert into each one of the one clavicle and one acromion tunnels;
    passing one flexible construct through each of the one clavicle and one acromion tunnels so that ends of the one flexible construct exit the other of the one clavicle and one acromion tunnels, respectively;
    placing one attachment device within or onto one of the one clavicle and one acromion tunnels; and
    securing the flexible construct to the attachment device.

13. The method of claim 12, wherein:
    the step of placing the one attachment device is after the step of securing the one cannulated insert.

* * * * *